US012636177B2

(12) United States Patent
Mandell et al.

(10) Patent No.: US 12,636,177 B2
(45) Date of Patent: May 26, 2026

(54) SYSTEM AND METHODS FOR A HIP JOINT REDUCTION PROCEDURE

(71) Applicant: University of Massachusetts, Boston, MA (US)

(72) Inventors: Daniel Mandell, Worcester, MA (US); Jonathan Nadler, Cambridge, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 35 days.

(21) Appl. No.: 16/965,484

(22) PCT Filed: Jan. 31, 2019

(86) PCT No.: PCT/US2019/016033
§ 371 (c)(1),
(2) Date: Jul. 28, 2020

(87) PCT Pub. No.: WO2019/152639
PCT Pub. Date: Aug. 8, 2019

(65) Prior Publication Data
US 2021/0052410 A1 Feb. 25, 2021

Related U.S. Application Data

(60) Provisional application No. 62/624,425, filed on Jan. 31, 2018.

(51) Int. Cl.
*A61F 5/01* (2006.01)
*A61F 5/042* (2006.01)
(Continued)

(52) U.S. Cl.
CPC ............ *A61F 5/0193* (2013.01); *A61F 5/042* (2013.01); *A61F 5/0585* (2013.01); *A61F 5/3761* (2013.01); *A61G 13/009* (2013.01)

(58) Field of Classification Search
CPC ...... A61F 5/0193; A61F 5/042; A61F 5/0585; A61F 5/3761; A61F 5/0109;
(Continued)

(56) References Cited

U.S. PATENT DOCUMENTS 3,612,042 A 10/1971 Fry
3,843,979 A * 10/1974 Treace .................. A61F 5/0585
5/651
(Continued)

FOREIGN PATENT DOCUMENTS

WO 2019/152639 A1 8/2019

OTHER PUBLICATIONS

PCT International Search Report and Written Opinion for International Application No. PCT/US2019/016033, entitled "System and Methods for a Hip Joint Reducation Procedure," mailed on Apr. 30, 2019, consisting of 7 pages.
(Continued)

*Primary Examiner* — Alireza Nia
*Assistant Examiner* — Robin Han
(74) *Attorney, Agent, or Firm* — Hamilton, Brook, Smith & Reynolds, P.C.

(57) ABSTRACT

The invention is directed to a system and methods to reduce a hip joint dislocation. Embodiments of the system may include a unitary or multipartite leg support assembly having about a 90-degree bend that is shaped to accommodate a leg, a lifting component, and a component for securing a leg to the leg support assembly. Embodiments of the multipartite leg support may be adjustable to accommodate any leg length. Embodiments of the system provide a mechanical advantage that may be used to reduce the hip joint, while simultaneously decreasing the possibility of injury to the user.

6 Claims, 3 Drawing Sheets

(51) Int. Cl.
    *A61F 5/058*         (2006.01)
    *A61F 5/37*          (2006.01)
    *A61G 13/00*        (2006.01)

(58) Field of Classification Search
    CPC .... A61F 2005/0183; A61F 5/048; A61F 5/05;
                A61F 5/01; A61F 5/04; A61F 5/058;
                A61F 5/05816; A61F 5/05833; A61F
               5/05841; A61F 5/37; A61F 5/3769; A61F
               5/3792; A61G 13/0081; A61G 13/123;
               A61G 13/1245; A61G 13/12; A61G
             13/0036; A61G 13/009; A61G 13/1205;
            A61H 1/0218; A61H 1/0229; A61H 1/02;
              A61H 1/0255; A61H 1/0237; A61H
                      1/0244; A61H 1/125
    USPC .............. 602/23, 32, 36, 33; 5/648; 128/892
    See application file for complete search history.

(56)            References Cited

U.S. PATENT DOCUMENTS 4,621,625 A  *  11/1986  Powlan ..................... A61F 5/04
                                        602/33
    4,817,588 A      4/1989  Bledsoe 5,575,765 A  *  11/1996  Foster .................... A61H 1/008
                                     606/241
    6,932,783 B1 *  8/2005  Donato ................. A61F 5/0193
                                      5/624
    2005/0085350 A1   4/2005  Shen
    2005/0178393 A1 * 8/2005  Bentley, II ............. A61G 13/12
                                     128/892
    2006/0100562 A1 * 5/2006  Pamplin ................ A61F 5/0193
                                     602/32
    2017/0143527 A1 * 5/2017  Paulos ............ A63B 21/00069

OTHER PUBLICATIONS

Extended European Search Report for EP 19 74 8098 dated Oct. 6, 2021, titled System and Methods for a Hip Joint Reduction Procedure.

* cited by examiner

SYSTEM AND METHODS FOR A HIP JOINT REDUCTION PROCEDURE

CROSS-REFERENCE TO RELATED APPLICATIONS

This application is the U.S. National Stage of International Application No. PCT/US2019/016033, filed Jan. 31, 2019, which designates the U.S., published in English, and claims the benefit of U.S. Provisional Application No. 62/624,425, filed Jan. 31, 2018. The entire teachings of the above applications are incorporated herein by reference.

FIELD OF INVENTION

The present invention relates generally to orthopedic devices. More specifically, the invention relates to a system and methods that may be used to facilitate a hip joint reduction procedure.

BACKGROUND OF THE INVENTION

The hip joint—a ball-and-socket joint—is formed of the upper end of the femur (thighbone)—otherwise known as the femoral head—and a cup-shaped cavity in the pelvis into which the femoral head fits—known as the acetabulum. The femoral head is connected to the femur by a neck region that is angularly disposed relative to the generally vertically aligned femoral axis. Any force applied through the femoral neck and head—such as through any impact that may be caused by walking, running, or jumping—may be transmitted through the femoral neck, through the acetabulum, and into the pelvis. If a person is subjected to great impact forces—such as if the person is in a car collision or falls from an elevated position—the resultant high stress and shear loads directed to the hip joint may force the femoral head out of the acetabulum and cause what is termed "hip joint dislocation". Severe cases of hip joint dislocation may also produce nerve, muscle, and ligament damage, as well as deterioration of cartilage located on the femoral head due to decreased blood supply, a condition known as avascular necrosis.

Hip joint dislocations are treated typically in emergency departments or an operating room at a hospital. There, a physician may treat the hip joint dislocation by repositioning the femoral head back into the acetabulum through a procedure known as hip joint reduction.

A hip joint reduction procedure may be either "open" or "closed". An "open" hip joint reduction includes an invasive surgical procedure that clears the acetabulum of muscle and/or connective tissue so that the femoral head may be reinserted into the acetabulum. "Closed" hip joint reductions are more common and require, for example, a physician to manipulate the leg and hip joint in order to reposition the femoral head into the acetabulum.

The "Allis Maneuver" is one way of accomplishing a closed hip joint reduction. In an Allis Maneuver, a patient is positioned in a supine position on a flat surface, such as a bed or gurney. The physician—in many instances, standing over the patient—must firmly grasp and flex the disarticulated leg at the knee to 90 degrees while simultaneously applying force to the leg. The physician may then gently extend the hip and externally rotate the leg to facilitate re-entry of the femoral head into the acetabulum.

The Allis Maneuver, while effective in reducing the hip joint, may have a number of disadvantages associated with it. First, the Allis Maneuver may require the physician to stand or kneel on a flat surface—such as hospital bed—to lift the patient's leg. This may place the physician in a physically awkward position, potentially leading to the loss-of-balance and a fall by the physician onto either the patient or the floor.

Another disadvantage of the Allis Maneuver is that the procedure may require a large amount of physical strength to manipulate and, ultimately, to reduce the hip joint. A physician of small stature, however, may be unable to apply the proper amount of force to either lift and hold the leg and/or to manipulate the leg to reduce the hip joint dislocation of a large patient. As a result, the physician may be unable to accomplish the procedure. Moreover, the physician—either due to having to adopt a physically awkward position or potentially having to apply a large amount of force to the leg—may incur a physical injury, such as a strained back, while attempting the procedure.

Further, the Allis Maneuver requires the application of force in a near vertical axis, that is, perpendicular and upward relative to the bent knee. However, due to the physician being in an awkward position on the flat surface, or by potentially slipping, such force may not be applied directly upward, or the force accidentally may be applied to a side of the knee. This may lessen the likelihood that the maneuver is performed correctly. Further damage to the hip joint or knee may be caused also.

Previous efforts to overcome these disadvantageous include the use of devices to help the physician perform the Allis Maneuver. For example, Bentley et al., US Pat. Pub. No. 2005/0178393A1 discloses an automated lifter arm and base intended to assist the physician in raising and manipulating the leg and hip. However, such a device may be too large and bulky for a hospital room. Moreover, such a device may be difficult to operate, as well as to store when not in use.

Accordingly, there is a need for a system and methods by which a hip joint reduction may be accomplished. The present invention satisfies this need.

SUMMARY OF THE INVENTION

Certain embodiments of the invention are directed to a system and methods to reduce a hip joint dislocation that include the use of an apparatus configured to support a disarticulated leg—while simultaneously providing an upward force on the leg—to assist the physician in manipulating, and, ultimately, reducing the dislocated hip joint.

Certain preferred embodiments of a system of the invention include a leg support assembly that is sized and shaped to support a leg. The leg support assembly may include an angled component configured to place the patient's leg in a bent position at the knee such that the calf area rests substantially perpendicular to the axis of the thigh. In certain preferred embodiments of the system, the angled component may be substantially 90-degrees or 90-degrees to allow the patient's leg to comfortably rest in the leg support assembly.

Certain embodiments of a system of the invention may further include one or more components for securing a leg that is positioned in the leg support assembly. The securing components may include one or more straps, or other known fasteners, by which the patient's leg may be releasably secured to the leg support assembly. Preferred embodiments of the invention include one or more straps having hooks and teeth—known commercially as Velcro®—that attach through openings or slots in the leg support assembly. The openings may be sized and shaped to allow a physician to thread the securing components through the openings to secure the leg.

Embodiments of a system of the invention may include a lifting component configured to lift the leg support assembly that supports the patient's leg. Embodiments of the lifting component may include one or more elements—such as gears, ratchets, sprockets, sheaves, axles, and the like—that may provide the physician with a mechanical advantage in lifting the leg support assembly supporting the leg and may also provide an upward force to facilitate or accomplish a hip joint reduction. In certain preferred embodiments, the lifting component may be a pulley system which allows the physician to exert a minimal downward force on a component of the pulley to lift and support the leg in the leg support assembly in an elevated position.

In order to secure a lifting component to the leg support assembly, certain embodiments of a system of the invention may include a coupling component. One preferred embodiment of a coupling component includes a body portion and one or more arms extending from the body portion. The one or more arms of the coupling component may be removably connected to the leg support assembly through the connection points. Further, the body portion of the coupling component may be removably connected to a lifting component to provide an even distribution of support to the leg support assembly. In one certain preferred embodiment of the system, the coupling component is a bale.

Certain preferred embodiments of a system of the invention may include one or more connection points. The connection points preferably are disposed on each side of the leg support assembly at or near the angled component to receive the coupling component in order to distribute evenly the upward lifting force of the system to the leg support assembly. The connecting points may include a hole, hook, clamp, or other fastener and may serve as an attachment point to a coupling component.

Alternate embodiments of a system of the invention may include an adjustable multipartite leg support assembly that may be constructed of two or more separate members. For example, one certain embodiment of the multipartite leg support assembly may include three separate members including a proximal member, a middle member, and a distal member. The middle member includes an angled component to allow a leg in the leg support assembly to bend at the knee. The proximal member and the distal member—which may be substantially straight and perpendicular to one another—support the thigh and calf, respectively.

Certain embodiments of a system of the invention having a multipartite leg assembly may include one or more tracks disposed along the length of the leg support assembly configured to interconnect each member of the multipartite leg assembly. This configuration allows the physician to adjust each member of the multipartite leg assembly to receive and secure the patient's leg. Preferably, two tracks connect the proximal portion to the middle portion and two tracks connect the distal portion to the middle portion.

In one certain embodiment of a system of the invention, the one or more tracks may be a linear rack with teeth to facilitate the movement and/or adjustment of the tracks.

Embodiments of a system of the invention having a multipartite leg assembly also may include a locking mechanism to secure the tracks in position after the individual leg support assembly portions are adjusted to a desired length to accommodate a leg. A locking mechanism may include one or more components such as removable clamps, bolts, pin, buckles, latches, or the like by which the leg support assembly may be locked in position. In preferred embodiments, the locking mechanism may be a pawl used in connection with the linear rack with teeth.

Any disclosed embodiments of a system of the invention may be used to perform a hip joint reduction procedure. According to one preferred embodiment of a method of the invention, the physician positions the patient on their back and secures the patient's leg in the leg support assembly. Next, the physician may operate the lifting component to exert an upward force on the leg support assembly. Once the desired height of the leg support assembly is reached, the physician may manipulate the leg and/or use the lifting force of the system to reduce the hip joint.

Advantageously, using the mechanical advantage provided by embodiments of a system of the invention, the physician may easily apply the force necessary to lift the leg support assembly and to reduce the hip joint. For example, embodiments of a system of the invention may require the physician to exert only a minimal downward force on the lifting component—such as a pulley—to lift the leg support assembly. This action eliminates the need for the physician to exert a strong upward force on the leg that may potentially lead to back injury.

Advantageously, the lifting component may be configured to attach to the leg support assembly at the angled component. In this configuration, the angled component may be vertically aligned with the lifting component and an anchor point that secures the lifting component to a support structure. This assures the force applied to the leg support assembly during the hip joint reduction is directly upward instead of—as may occur in the Allis Maneuver and the like—to a side of the leg that may cause further injury to the patient.

A further advantage of a system of the invention includes the ability to configure the leg support assembly in order to fit legs of various lengths.

In still further advantages, embodiments of the system of the invention—when in use—may attach to any anchor point in an emergency room such as a ceiling or other support frame. Moreover, the system may easily be removed from the anchor point and stowed away.

The present invention and its attributes and advantages will be further understood and appreciated with reference to the detailed description below of presently contemplated embodiments, taken in conjunction with the accompanying drawings.

BRIEF DESCRIPTION OF THE DRAWINGS

The preferred embodiments of the invention will be described in conjunction with the appended drawings provided to illustrate and not to the limit the invention, where like designations denote like elements, and in which.

DETAILED DESCRIPTION OF THE INVENTION

Figure 1:
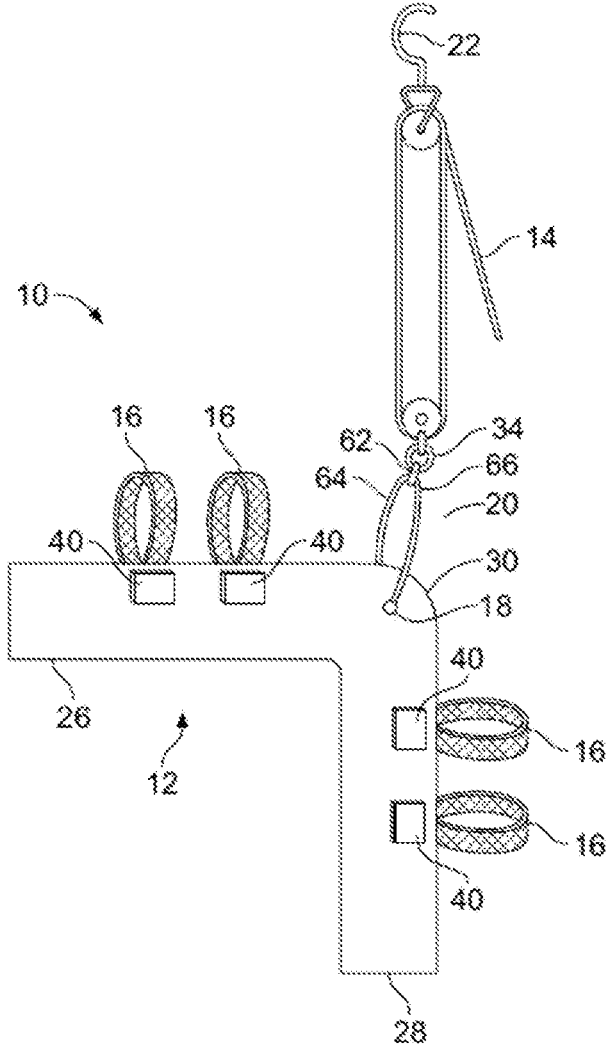
FIG. 1 illustrates a side view of an embodiment of a hip joint reduction system.

The present invention is directed to a system and methods of performing a hip joint reduction procedure. One preferred embodiment of a system of the invention is illustrated in FIG. 1. The system 10 includes a leg support assembly 12, a lifting component 14, one or more securing components 16, one or more connection points 18, a coupling component 20, and a lifting component support element 22.

Certain embodiments of a system of the invention include the use of a leg support assembly 12 having a "U" shaped body with an inner surface 24 having a continuous "U" shaped wall defining an inner space and configured to receive and support at least a portion of a patient's leg extending from the dislocated hip joint. The leg support assembly 12 may be a unitary leg support having an angled component 30 between a first substantially straight member 28 and a second substantially straight member 26. When positioned in the leg support assembly 12, the patient's leg may bend at the angled component 30 while the thigh rests in the first substantially straight member 28 and the calf rests in the second substantially straight member 26. As used in this Application, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

In certain embodiments of a system of the invention, the angled component 30 may be bent at an angle of about 80-degrees to about 100-degrees. In some embodiments of the system, the angled component 30 may be bent at about 90-degrees. One certain preferred embodiment of the system may include an angled component 30 bent at 90-degrees. For purposes of this Application, the term "about" refers to an approximately +1-10% variation from a given value. It is to be understood that such a variation is always included in any given value provided herein, whether or not it is specifically referred to, unless stated otherwise The leg support assembly 12 may be constructed of any light weight and easy to clean material such as fiberglass, plastic, thermoplastics, metal. Or a combination thereof. The leg support assembly 12 also may include a material 48 lining the inner wall 24 of the leg support assembly 12 to further support the patient's leg. Suitable liner materials include neoprene, foam, or a gel-filled support material.

Certain embodiments of the system of the invention also may include a lifting component 14 configured to provide a mechanical advantage used to lift and hold the weight of the leg in the leg support assembly 12 and allow the physician to manipulate the leg positioned in the leg support assembly. Embodiments of the lifting component 14 may include gears, ratchets, sprockets, sheaves, axles, and the like. In certain preferred embodiments, the lifting component may be a rope and pulley system or belt and pulley system.

Pulley systems—also known as a block and tackle—may be classified as fixed, movable, or compound pulley systems. A fixed pulley system may include one or more axles mounted in bearings and attached to an anchor point or supporting structure. A movable pulley system may include one or more axles in a movable block. A compound pulley system may include a combination of at least one fixed pulley and at least one movable pulleys. A physician may determine the type of pulley system required to provide the necessary mechanical advantage to accomplish the hip reduction procedure.

Certain embodiments of a system of the invention also may include a lifting component support element 22, 66. The lifting component support element 22 may be attached to, or integral to the lifting component 14 and may be used to secure the lifting component 14 to an anchor point such as a ceiling or support frame. The lifting component support element 22 may include a chain, carabiner, hook, clasp, or other fastener.

In certain embodiments of a system of the invention, a coupling component 20 may be disposed between the leg support assembly 12 and the lifting component 14. The coupling component 20 may include any type of fastener such as a hook, clasp, carabiner that may support the weight of the patient's leg in the leg support assembly 12.

In one preferred embodiment of a system of the invention, the coupling component 20 may be a bale. A bale may include, for example, a body portion 62 and one or more support arms 64, 66 extending from the body portion. The bale may be shaped as a "horse-shoe" or "wish bone" such that the body portion 62 may be connected to the lifting component 14 through a hook, clasp, or other fastener 34, and the two arms 64, 66 extending from the body portion may be configured to attach to the leg support assembly 12 at or near the angled component 30 to distribute the applied upward force more evenly to the leg support assembly 12.

Certain embodiments of a system of the invention include connection points 18 sized and shaped to receive the coupling component 20. Connection points 18—located at or near the angled component 30—may include holes, or reinforced holes having increased layers of material, or a metal support, that may directly engage the coupling component 20. In certain embodiments of the system, the connection points 18 are rotatable and joinable to the coupling component 20. This configuration facilitates movement of the leg support assembly during the hip joint reduction procedure. The connection points 18 also may be positioned directly opposite one another on an outside surface of the angled component 30.

Certain embodiments of a system of the invention also may include one or more components for securing a leg 16 to the leg support assembly 12. The components for securing the leg 16 to the leg support assembly 12 may be, for example, a strap or clasp extending from a first side of the leg support assembly 12, over the leg, and to a second side of the leg support assembly 12. The straps may be removable and may be inserted or threaded into an opening 36 in the leg support assembly 12. In preferred embodiments of the system, the components for securing a leg 16 to the leg support assembly 12 includes one or more straps having hooks and teeth, such as Velcro® straps. The components for securing a leg 16 to a leg support assembly 12 also may include synthetic, leather, or canvas straps, woven thread webbing, ties, wires, strap and buckle, and metal or polymer bars in addition to, or in place of the Velcro® straps.

Figures 2A, 2B, 2C:
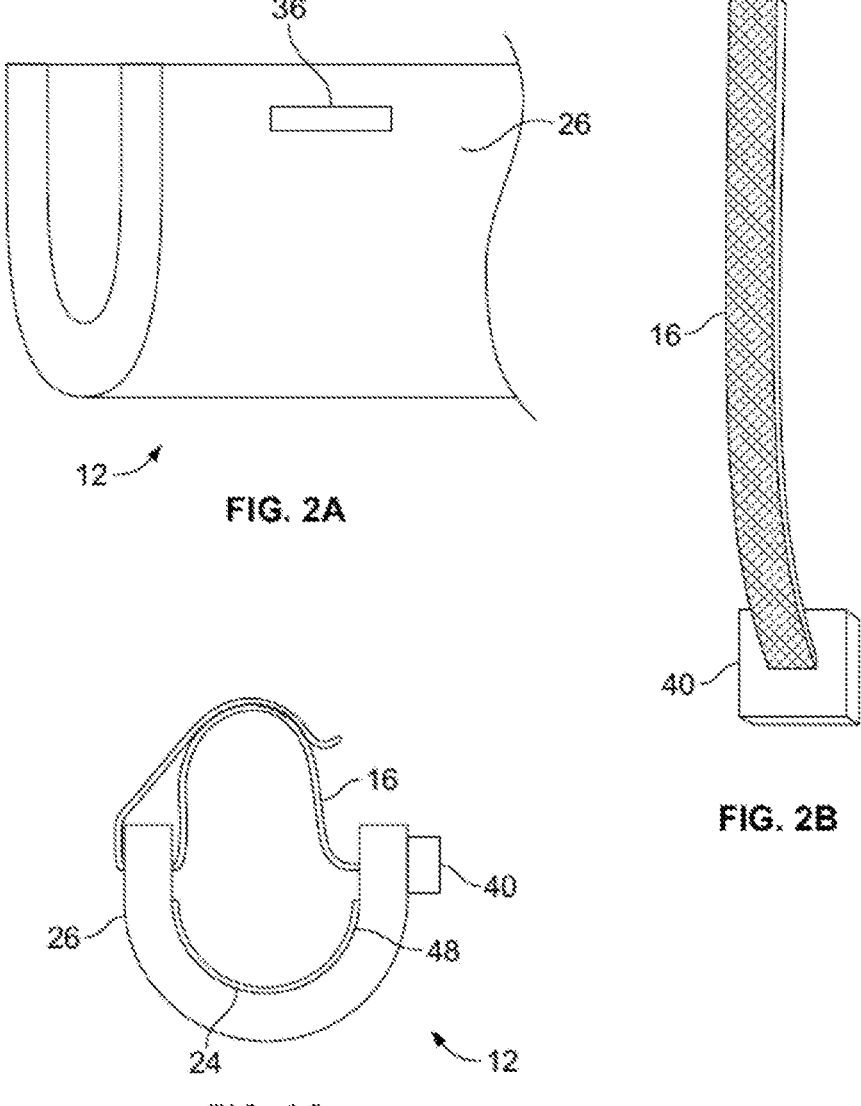
FIG. 2A illustrates a side view of an embodiment of the invention having attachment slots for certain components for securing a leg to the leg support assembly.
FIG. 2B illustrates embodiments of the securing components having a strap and stopper element.
FIG. 2C illustrates a front view of the leg support assembly shown in FIG. 2A having a strap and stopper element.

FIG. 2A-C illustrates certain embodiments of the components for securing a leg 16 to a leg support assembly 12. FIG. 2A illustrates the distal end of the second substantially straight member 26 of a leg support assembly 12 having openings 36 on either or both sides of the "U" shaped leg assembly. FIG. 2B illustrates certain components for securing a leg 16 to a leg support assembly—in this case, a strap—that also may include a stopper element 40 disposed at one end of the strap 16. As is further illustrated in FIG. 2C, in use, the strap 16 may be threaded through each of the openings 36 of the leg support assembly 12 such that the stopper element 40 abuts the outside surface of the leg support assembly 12 and is prevented from further forward movement through opening 36. The strap 16 may then secure the leg inside the "U" shaped space of the leg support assembly 12.

Alternate embodiments of a system 70 of the invention may include a multipartite leg support assembly 60 constructed of two or more separate members, one or more components for securing a leg 16 to the multipartite leg support assembly 60, one or more connection points 18, a lifting component 14, a coupling component 20, and a lifting component support element 22.

Figure 3:
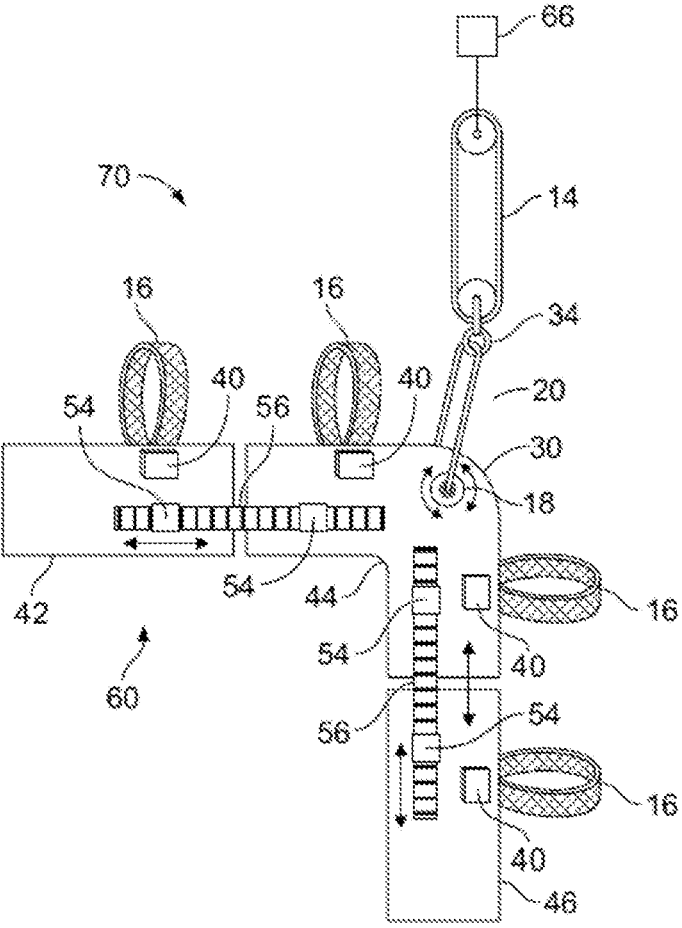
FIG. 3. illustrates a side view of an embodiment of a hip joint reduction system having a multipartite leg support assembly.

One certain preferred embodiment of a system of the invention is illustrated in FIG. 3. The system 70 includes a multipartite leg support assembly 60 having at least three separate members: a distal member 42, a middle member 44, and a proximal member 46. The middle member 44 of the multipartite leg support assembly 60 includes an angled component 30 of about 90-degrees to allow a patient's leg positioned in the multipartite leg support assembly 60 to bend at the knee. The proximal member 44 and the distal member 46 may be substantially perpendicular to one another, and each of the proximal member 44 and the distal member 46 connected to the middle member 44 through track system 56.

Certain embodiments of a system of the invention include an adjustable linear track system 56. In addition to connecting each of the members 42, 44, 46 of the multipartite leg support assembly 60 together, the track system 56 allows a physician to slidably adjust the multipartite leg support assembly 60 to accommodate a leg of any length (direction of movement shown by arrows). While the track system 56 may include any type of rod, track, or rail, preferably, the track system 56 includes a linear rack with teeth and/or a gear or ratchet system. Other adjustment means may include a mechanism that may be threaded or non-threaded, and which may be engaged by the action of a screw or worm screw, a friction mechanism, a friction-detent mechanism, a toothed mechanism, a gear mechanism, a ratchet mechanism, a rack and pinion mechanism, or such other devices to permit discreet adjustment and retention of a desired length and position of the multipartite leg support assembly 60.

Embodiments of a system of the invention having the multipartite leg support assembly 60 also may include a locking mechanism 54 to secure the track system 56 and leg support members 42, 44, 46 in place after adjustment. Suitable locking mechanisms include adjustable clamps, brackets, buckles, ties, pawls, or removable bolt and screws. In preferred embodiments of the invention, the locking mechanism 54 may be a pawl. Preferably, at least a portion of the track system 56 fits into and may pass through a slot or bracket of the locking mechanism 54 sized and shape to receive the track system 56. The track system 56 may be ratcheted or otherwise adjusted and moved through the locking mechanism 54 and secured, for example, with a pawl under spring tension or other mechanism configured to engage the teeth of the track system 56. The pawl or other mechanism may be disposed, for example, on a bracket through which the track passes to engage the teeth of the track system 54. In other embodiments of the invention, the track system 56 may include teeth on one or more surfaces of the track that engage complementary teeth disposed on the surface of the multipartite leg support assembly 60 and secured together after adjustment to a proper length through the use of one or more brackets, buckles, pawls, or other locking mechanisms.

Embodiments of the system of the invention may be used to facilitate or accomplish a hip joint reduction procedure. In a preferred embodiment of a method of the invention, a physician—after securing the patient's leg in the leg support assembly 12—may apply upward lifting force to the leg and hip through the leg support assembly 12 using the lifting component 14. After lifting the leg support assembly 12 to a desired height, the physician may manipulate the leg and hip. If needed, the physician also may apply additional upward force to the leg support assembly 12 through the lifting component 14 to accomplish the hip joint reduction.

In further embodiments of a method of the invention, the physician may adjust the multipartite leg support assembly 60 to fit any length of leg such as a child's leg or an adult's leg. In such embodiments, the leg support assembly 60 may be made longer or shorter by slidably adjusting the distal leg support portion 42 along the track connecting 56 the distal leg support portion 42 to the middle leg support portion 44, or the proximal leg support portion 46 to the middle portion 44, or both. After the leg support members 42, 44, 46 are satisfactorily adjusted, the various members may be secured in place through actuation of locking mechanism 54. The leg support assembly 60 may then be lifted—using the mechanical force supplied by the system—to gently manipulate the patient's femoral head or prosthetic ball into the hip joint to complete the hip joint reduction procedure.

The singular forms "a," "an," and, "the" include plural referents unless the context clearly dictates otherwise. Thus, for example, reference to "a boot" includes reference to one or more of such boots, and reference to "the attachment" includes reference to one or more of such attachments.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described in the Application are to be taken as examples of embodiments. Elements and materials may be substituted for those illustrated and described in the Application, parts and processes may be reversed, and certain features of the invention may be utilized independently, all as would be apparent to one skilled in the art after having the benefit of this description of the invention. Changes may be made in the elements described in the Application without departing from the spirit and scope of the invention as described in the following claims.

What is claimed is:

1. A system for reducing a disarticulated leg from a dislocated hip joint comprising:

a leg support assembly sized and shaped to support the disarticulated leg, said leg support assembly having a first member configured to engage a thigh of the disarticulated leg and a second member configured to engage a calf of the disarticulated leg, the first member and the second member merged at an angled component fixedly bent at about 90-degrees, the angled component constructed of an inflexible material;

one or more components for securing the disarticulated leg to said leg support assembly, said one or more components for securing the disarticulated leg removably attached to said leg support assembly;

a connection point formed directly on the leg support assembly at said angled component bent at about 90-degrees;

a lifting component support element having a fastener configured to be secured to an anchor point;

a coupling component;

a lifting component having a first end and a second end, wherein the first end is removably attached to said lifting component support element, the second end is configured to be removably attached to said coupling component, said coupling component including one or more arms, the one or more arms are removably attached to the connection point, and wherein the lifting component is constructed and arranged to provide a mechanical advantage used to lift the leg support assembly in a direction that is directly upward, perpendicular to the second member and hold the leg support assembly; and said lifting component is configured to apply an upward force to the leg support assembly directly and solely at the connection point and in a direction of a longitudinal axis of the first member to lift the disarticulated leg in said leg support assembly to accomplish a hip joint reduction procedure.

2. The system of claim 1, said leg support assembly further including an inner surface and an outer surface, the inner surface containing a liner material disposed on at least a portion of said inner surface.

3. The system of claim 1, wherein said lifting component is a pulley mechanism.

4. The system of claim 1 further comprising one or more openings disposed along a length of said leg support assembly and configured to receive said one or more components for securing the disarticulated leg.

5. The system of claim 1, wherein said one or more components for securing the disarticulated leg include straps having teeth and hooks.

6. The system of claim 1, wherein said leg support assembly is a unitary leg support assembly.

* * * * *